United States Patent [19]

Kyle

[11] 4,421,947

[45] Dec. 20, 1983

[54] POLYCRYSTALLINE INSULATING MATERIAL SEALS BETWEEN SPACED MEMBERS SUCH AS A TERMINAL PIN AND A FERRULE

[75] Inventor: James C. Kyle, 24372 Via San Clemente, Mission Viejo, Calif. 92675

[73] Assignee: James C. Kyle, Roseburg, Oreg.

[21] Appl. No.: 229,151

[22] Filed: Jan. 28, 1981

Related U.S. Application Data

[63] Continuation of Ser. No. 840,740, Oct. 11, 1977, abandoned.

[51] Int. Cl.$^3$ .............. H01B 17/26; C03C 27/02; C03C 3/22
[52] U.S. Cl. .............. 174/152 GM; 65/33; 65/59.34; 65/59.35; 65/59.5; 128/419 P; 403/30; 501/4; 501/15; 501/76
[58] Field of Search .............. 174/50.58, 50.61, 50.63, 174/151, 152 GM; 65/33, 36, 42, 59.1, 59.3, 59.31, 59.34, 59.35, 59.4, 59.5, 59.6; 128/419 P; 228/122, 903; 403/28, 29, 30, 179; 428/432, 433, 434

[56] References Cited

U.S. PATENT DOCUMENTS

| | | | |
|---|---|---|---|
| 3,113,878 | 12/1963 | Martin | 65/33 X |
| 3,141,753 | 7/1964 | Certa | 65/59.34 X |
| 3,199,967 | 8/1965 | Pixley | 174/152 GM X |
| 3,225,132 | 12/1965 | Baas et al. | 174/151 |
| 3,258,350 | 6/1966 | Martin et al. | 174/50.61 X |
| 3,485,648 | 12/1969 | Bishop | 65/33 X |
| 3,920,888 | 11/1975 | Barr | 174/152 GM |
| 3,951,669 | 4/1976 | Malmendier et al. | 501/4 |
| 3,963,505 | 6/1976 | Dumesnil et al. | 501/15 |
| 4,022,627 | 5/1977 | Tashiro et al. | 501/4 |
| 4,047,292 | 9/1977 | Shaffer | 174/152 GM X |
| 4,097,296 | 6/1978 | Thomas et al. | 501/15 |

FOREIGN PATENT DOCUMENTS 962115 6/1964 United Kingdom .............. 501/4

Primary Examiner—Laramie E. Askin
Attorney, Agent, or Firm—Ellsworth R. Roston; Charles H. Schwartz

[57] ABSTRACT

A material hermetically seals two members. One member may be titanium or a titanium alloy and the other member may be a noble metal such as platinum. The seal is resistant to acids and alkalis and is substantially impervious to shocks resulting from mechanical forces or abrupt changes in temperature. The material includes a pair of fluxes having different melting temperatures and a stuffing material including the oxides of zinc and zirconium. The oxides of zinc and zirconium become crystallized at the surface between one of the members and the material. An oxygen valence bond is also produced between the material and such member. The material is more amorphous at the boundary with the second member than at positions removed from such member. The material is formed by progressive heatings for at least a pair of periods of time insufficient to crystallize all of the material and by rapid coolings of the material after each of such heatings.

61 Claims, 9 Drawing Figures

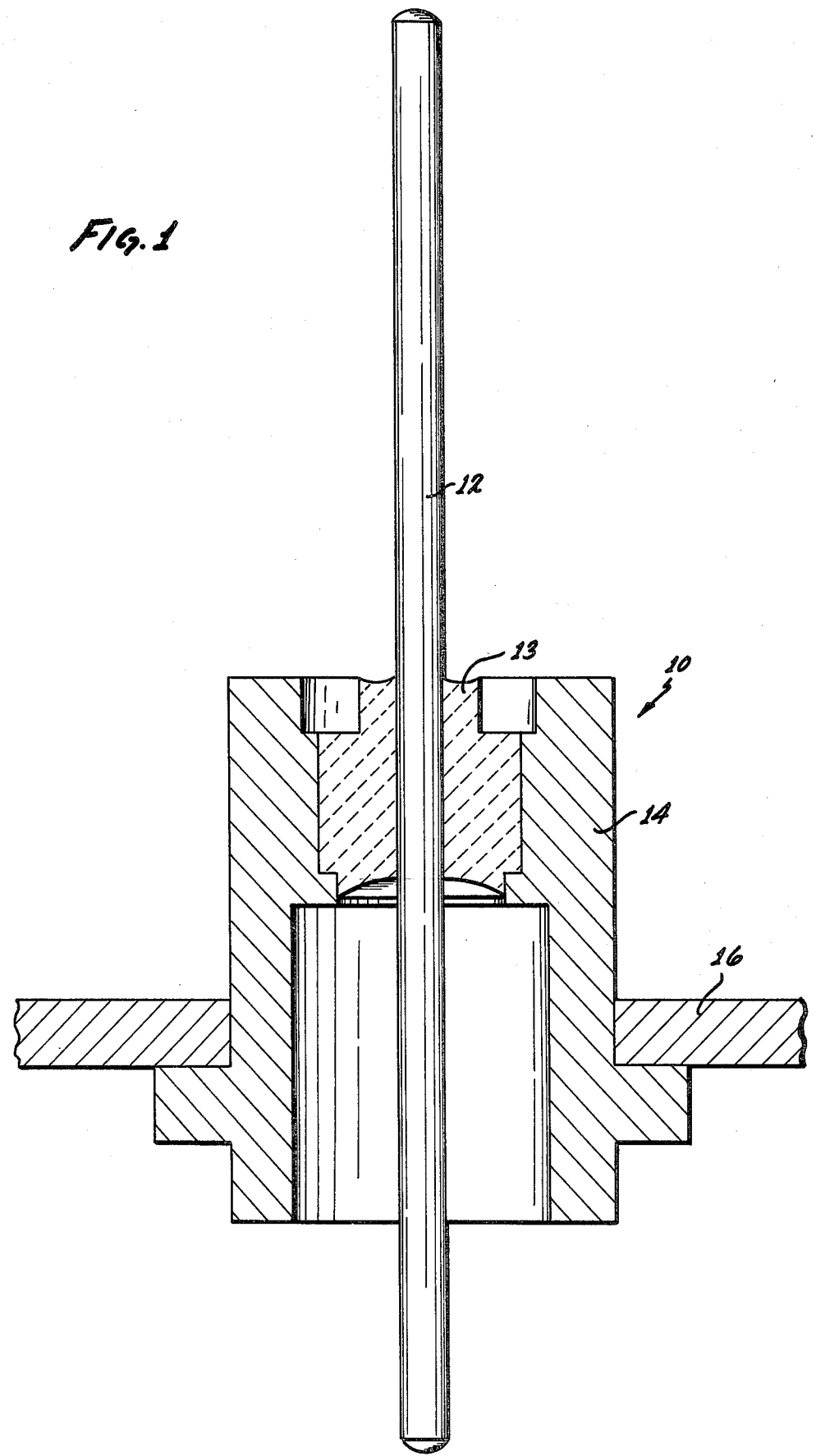

FLUX A

| MATERIAL | RELATIVE PERCENTAGE BY WEIGHT |
|---|---|
| LEAD OXIDE (PbO) | 68.5 |
| BORIC OXIDE ($B_2O_3$) | 10.5 |
| SILICON DIOXIDE ($SiO_2$) | 21.0 |

FIG. 2

FLUX B

| MATERIAL | RELATIVE PERCENTAGE BY WEIGHT |
|---|---|
| LEAD OXIDE (PbO) | 80 |
| BORIC OXIDE ($B_2O_3$) | 20 |

FIG. 3

FIG. 4

OTHER FLUXES

| MATERIAL | FLUX C | FLUX D | FLUX E | FLUX F | FLUX G |
|---|---|---|---|---|---|
| LEAD OXIDE (PbO) | 81.8 | 78.8 | 66.6 | 55.5 | 48.6 |
| BORON OXIDE ($B_2O_3$) | 10.6 | 9.6 | 18.6 | 3.0 | 6.9 |
| SILICON DIOXIDE ($SiO_2$) | 7.6 | 11.6 | 14.8 | 29.6 | 25.0 |
| SODIUM OXIDE ($Na_2O$) | | | | 4.4 | 3.6 |
| TITANIUM DIOXIDE ($TiO_2$) | | | | 4.0 | 2.4 |
| LITHIUM OXIDE ($Li_2O$) | | | | | 3.6 |
| ZIRCONIUM DIOXIDE ($ZrO_2$) | | | | | 6.7 |

CHARACTERISTICS

| | | | | | |
|---|---|---|---|---|---|
| MELTING POINT (°F.) | 850 | 950 | 1050 | 1140 | 1120 |
| COEFFICIENT OF THERMAL EXPANSION (IN/IN $\times 10^{-7}$) | 104 | 85 | 76 | 90 | 85 |

CRYSTAL STUFFING

| MATERIAL | RELATIVE PARTS BY WEIGHT |
| --- | --- |
| LEAD ANTIMONATE $(Pb_3(SbO_4)_2)$ | 2 |
| ZINC ZIRCONIUM SILICATE | 1 |
| ZIRCONIUM SPINEL | 1 |
| ZIRONIUM SILICATE | 1 |

FIG. 5

CRYSTAL STUFFING

| MATERIAL | RELATIVE PARTS BY WEIGHT |
| --- | --- |
| SILICON DIOXIDE $(SiO_2)$ | 33.3 |
| ZINC OXIDE $(ZnO)$ | 33.3 |
| COBALT OXIDE $(CoO)$ | 10.0 |
| ZIRCONIUM SILICATE $(ZrSiO_4)$ | 15.0 |
| MOLYBDIC OXIDE $(MoO_3)$ | 5.0 |

FIG. 6

FIG. 7

CRYSTAL STUFFING

| MATERIAL | RELATIVE PARTS BY WEIGHT |
| --- | --- |
| SILICON DIOXIDE | 20 |
| MOLYBDIC OXIDE | 4 |
| COBALT OXIDE | 3 |
| LEAD ANTIMONATE | 15 |
| ZINC OXIDE | 8 |
| ZIRCONIUM SILICATE | 30 |
| MAGNESIUM ZIRCONIUM SILICATE | 20 |

CRYSTAL STUFFING

| MATERIAL | RELATIVE PARTS BY WEIGHT |
|---|---|
| COBALT OXIDE | 31.3 |
| QUARTZ | 25.6 |
| ZIRCONIUM SPINEL | 14.2 |
| ZINC ZIRCONIUM SILICATE | 14.2 |
| TIN OXIDE | 14.2 |

FIG. 8

CRYSTAL STUFFING

| MATERIAL | RELATIVE PARTS BY WEIGHT |
|---|---|
| SODIUM ANTIMONATE | 10 |
| LEAD ANTIMONATE | 25 |
| MOLYBDIC OXIDE | 3 |
| SILICON DIOXIDE | 22 |
| TITANIUM DIOXIDE | 2 |
| ZINC ZIRCONIUM SILICATE | 38 |

FIG. 9

POLYCRYSTALLINE INSULATING MATERIAL SEALS BETWEEN SPACED MEMBERS SUCH AS A TERMINAL PIN AND A FERRULE

This is a continuation of application Ser. No. 840,740, filed Oct. 11, 1977, now abandoned.

This invention relates to materials which bond two particular metals and primarily titanium or alloys of titanium. The invention further relates to methods of producing such materials and further relates to methods of bonding such materials to the metals such as titanium and alloys of titanium and also of bonding the metals to noble metals such as platinum and to certain other materials such as certain nickel alloys, alumina, other ceramics and glasses so as to form a hermetic seal between these members.

Heart pacemakers employ electrical terminal pins made from a suitable noble metal such as platinum. These terminal pins are disposed within ferrules made from suitable metals including titanium or alloys of titanium such as alloys of titanium with vanadium and aluminum. The ferrules are disposed on the lid of the housing for the heart pacemaker and provide an electrical shielding for the terminal pin.

Electrical insulation is provided between the terminal pin and the ferrule. This insulation should be hermetically sealed to the ferrule and should be able to withstand considerable mechanical and temperature stresses. The insulation should be able to withstand strong acids and alkalis such as sometimes exist in the body of a patient and the material should provide a high electrical insulation between the terminal pin and the ferrule. The material should be provided with these characteristics since the heart pacemaker is disposed within the body of a patient and should be able to operate for long periods of time in the patient's body without any deterioration in the quality of its operation even under the most unusual circumstances.

A substantial effort has been devoted to provide a hermetic seal between the terminal pin and the ferrule in a heart pacemaker with the properties described above. Such efforts have not been successful. A successful seal has not been produced between the terminal pin and the ferrule by the insulations now in use, particularly when the ferrule has been made from titanium or a titanium alloy. Furthermore, the insulations now in use have not been able to withstand mechanical and temperature shocks and have not been resistant to strong acids and alkalis. As a result, heart pacemakers have had to be replaced in patients' bodies far more often than the patients would wish, with resultant discomfort and anxiety and even debilitation to the patient.

This invention provides a material which overcomes the disadvantages discussed above. The invention provides a hermetic seal between a pair of spaced members such as a terminal pin and a ferrule in a heart pacemaker, particularly when the ferrule is made from titanium or an alloy of titanium. The invention is substantially impervious to shocks resulting from mechanical forces or abrupt changes in temperature. The material has a high dielectric constant so that it provides a very high electrical insulation between the two members that it is hermetically sealing. The material does not propagate cracks, thereby maintaining its properties of providing a hermetic seal and a high electrical insulation even under adverse circumstances. The material is also resistant to strong acids and bases.

As will be appreciated, all of the properties discussed above are particularly beneficial when the material is hermetically sealing a terminal pin and a ferrule in a heart pacemaker, particularly when the terminal pin is made from a noble metal such as platinum and the ferrule is made from titanium or an alloy of titanium. All of the properties are particularly beneficial since the heart pacemaker is now generally disposed in the body of a patient when it has to function dependably under all of the adverse conditions that a human body sometimes produces under adverse circumstances.

The material of this invention is formed from a plurality of oxides some of which are alkaline and some of which are acidic. The material includes at least a pair of fluxes each including oxides of lead and boron, and one additionally including the oxide of silicon, and each having a melting temperature different from the melting temperature of the other flux. Preferably the melting temperatures of the fluxes differ by several hundred degrees from each other. The material of this invention further includes a stuffing material having properties of becoming crystalline when heated to an elevated temperature for an extended period of time. The stuffing material includes oxides of zinc and zirconium.

To form the material constituting this invention, each of the fluxes is initially melted and quenched in water. The fluxes are then mixed with the crystal stuffing and heated to a temperature of approximately 1200° F. for a relatively short period of time such as approximately two (2) to three (3) hours so as to be partially combined into a material which is primarily amorphous and partially crystalline. The material is then quenched in water and then is heated to a temperature of approximately 1100° F. which is slightly above the melting temperature of the material in this stage of formation. The material is heated at the temperature of approximately 1100° F. for a period which causes it to become progressively crystalline and to have a coefficient of thermal expansion slightly greater than those of the members that it will be sealing. The material is then formed into pellets and is disposed between the members that it will be sealing. The material and the members are then heated for a period of approximately one-half hour to a temperature of approximately 1225° F. to fuse the material to the member.

When one of the members to be sealed constitutes a ferrule made from titanium or an alloy of titanium, the material has a crystalline structure at the boundary with such member. The crystalline structure is formed by crystals of Willemite (a zinc silicate) and zirconium silicate. The Willemite crystals have a different size and shape than the crystals of zirconium silicate so that the crystalline structure at the boundary with the member can flex when subjected to thermal or mechanical shock. An oxygen valence bond is also produced between the member and the material of this invention to seal the member and the material.

The characteristics of the material can be adjusted by varying the temperature at which the material is heated in the steps described previously and by varying the time during which the material is heated. In this way, the coefficient of thermal expansion of the material can be adjusted so that it is slightly above the coefficient of thermal expansion of the member to be sealed. In this way, the material contracts slightly more rapidly during the cooling process than the member to be sealed so that a hermetic seal of optimal characteristics is produced between them. Furthermore, the material is more crystalline at the boundary with the member to be sealed than at positions removed from such boundary. This causes the material to have at these positions properties which provide for optimal adjustability between the material and the member when the material and the member experience unnatural stresses from temperature changes and mechanical forces.

In the drawings:

FIG. 1 is a simplified sectional view of a terminal for use in a heart pacemaker, the terminal including the material of this invention; and FIGS. 2 through 9 constitute charts showing the compositions of various materials included in this invention.

In one embodiment of the invention, a terminal generally indicated at 10 is provided for a heart pacemaker. A suitable embodiment of the terminal is disclosed by me in copending application Ser. No. 836,657 filed by me on Sept. 26, 1977, for Terminal for Medical Instrument, now U.S. Pat. No. 4,220,813, and assigned by me of record to the assignee of record of this application. The terminal includes a terminal pin 12 disposed in concentric relationship to a ferrule 14.

Preferably, the ferrule is made from a suitable material such as titanium or an alloy of titanium such as with vanadium and aluminum. The terminal pin 12 may be formed from a noble metal which is preferably platinum. However, other noble metals such as gold, silver, irridium and rhodium may also be used. The terminal pin 12 may also be formed from certain nickel alloys such as those designated by the trademarks "Rene 41" and "Inconel".

A suitable insulating material 13 is disposed between the terminal pin 12 and the ferrule 14 and is hermetically sealed to the terminal pin in the ferrule. Preferably the insulating material constitutes the material of this invention. The insulating material 13 insulates the terminal pin 12 from the ferrule 14 in a lid 16 of the heart pacemaker when the ferrule 14 is attached to the lid.

The material of this invention includes a pair of fluxes having different melting temperatures. Preferably one of the fluxes has a melting temperature greater by several hundreds of degrees Farenheit, such as approximately 200° F. to 300° F., than the other flux. By way of illustration, one of the fluxes (Flux A) may have a melting temperature of approximately 800° F. and a composition as follows:

| Material | Relative Percentage By Weight |
| --- | --- |
| Lead oxide (PbO) | 68.5 |
| Boric oxide ($B_2O_3$) | 10.5 |
| Silicon dioxide ($SiO_2$) | 21.0 |

The other flux (Flux B) may have a melting temperature of approximately 1000° F. and a composition as follows:

| Material | Relative Percentage By Weight |
| --- | --- |
| Lead oxide (PbO) | 80.0 |
| Boric oxide ($B_2O_3$) | 20.0 |

Fluxes A and B tend to constitute eutectics which effectively lower the melting point of the boric oxide in the fluxes.

When fluxes A and B are provided as specified above, Flux A may have a relative percentage by weight in the material of approximately fifteen percent (15%) to twenty-five percent (25%) and flux B may have a relative percentage by weight in the material of approximately forty percent (40%) to fifty-five percent (55%). A stuffing material having properties of becoming crystalline is also provided in the material in a percentage by weight of approximately twenty percent (20%) to forty-five percent (45%).

The crystal stuffing includes oxides of zinc and zirconium and silicon dioxide to provide for the formation of crystals in at least a portion of the material. The oxides of zinc and zirconium and the silicon dioxide may be included in such forms as zinc zirconium silicate, zirconium spinel and zirconium silicate. For example, the crystal stuffing may be formed from the following materials in the following percentages by weight:

| Material | Relative Parts by Weight |
| --- | --- |
| Lead antimonate ($Pb_3(SbO_4)_2$) composed of lead, antimony and oxygen | 2 |
| Zinc zirconium silicate | 1 |
| Zirconium spinel | 1 |
| Zirconium silicate | 1 |

The crystal stuffing specified above has particular utility in hermetically sealing pure titanium.

To form the material of this invention and to produce hermetic seals with such material, fluxes A and B are first smelted separately and quenched in water to frit the material. For example, flux A may be smelted for a period of approximately two (2) hours at a temperature of approximately 1500° F. and then quenched in water, and flux B may be smelted for a period of approximately one (1) hour at a temperature of approximately 1200° F. and then quenched in water. The crystal stuffing is smelted for a period of approximately three (3) hours at a temperature of approximately 1800° F. and is then quenched in water.

The fritted fluxes and the crystal stuffing are then mixed in the desired percentages and ground, such as in a ball mill, for a period of approximately three (3) to four (4) hours. The material is then heated to a temperature of approximately 1200° F. to 1300° F. for a period of approximately two (2) to three (3) hours. Preferably the material is stirred periodically, such as every fifteen (15) minutes, while it is being heated. The temperatures and times chosen for such heating operation are such as to partially combine the different compounds in the mixture. As a result, the material is predominantly amorphous but a portion has become crystalline. For example, approximately eighty percent (80%) of the material may be amorphous and approximately twenty percent (20%) may be crystalline. The material is then converted to a frit by quenching in water. The resultant material has a melting temperature of approximately 1100° F.

The material is then heated to a temperature slightly above its melting temperature for a period of time dependent upon the characteristics desired for the material. For example, the material may be heated to a temperature of approximately 1200° F. (100° F. above the melting temperature) for a period of approximately three (3) to four (4) hours. The material slowly changes from an amorphous glass to a ceramic as it is being heated. Furthermore, the coefficient of thermal expansion of the material slowly decreases as the material becomes progressively crystalline.

The temperature and duration of the heating operation are chosen so that the coefficient of thermal expansion of the material is slightly greater than the coefficient of thermal expansion of the member, such as the ferrule 14, to be sealed. The temperature and duration of the heating operation are such that the material is approximately fifty percent (50%) amorphous and approximately fifty percent (50%) crystalline or slightly more crystalline than amorphous.

The fritted material is then pulverized and separated into different sizes. Beads are then formed by mixing particles of different sizes with a suitable material such as polyethylene glycol (marketed under the name "Carbowax") or an animal fat and pressing the particles together. For example, approximately forty percent (40%) of particles by weight with 150 mesh, approximately fifty percent (50%) of particles with 300 mesh and approximately ten percent (10%) of particles above 300 mesh may be mixed with polyethylene glycol or an animal fat where the polyethylene glycol or the animal fat comprises one and one-half percent (1.5%) to three percent (3%) by weight in the mixture. The particles may then be pressed together to form the beads.

The beads are then disposed between the terminal pin 12 and the ferrule 14. The combination is then heated to a suitable temperature such as approximately 1225° F. for a suitable period of time such as a period to approximately thirty (30) minutes. The material then becomes fused to the terminal pin 12 and the ferrule 14. Since the combination is heated for only a relatively short period of time, the crystal structure of the material 13 is not changed significantly during the heating operation.

The fusion of the material 13 to the ferrule 14 is facilitated by cooling the material rapidly in air. This causes the material 13 to press against the ferrule 14 as it is rapidly cooled, particularly since the coefficent of thermal expansion of the material 13 is slightly greater than that of the ferrule 14. By pressing against the ferrule during such cooling, the material facilitates the production of a hermetic seal with the ferrule.

The hermetic seal between the material 13 and the ferrule 14 is produced in various ways. For example, a thin polycrystalline layer is produced in the material at the boundary with the ferrule 14. For example, zinc silicate ($Zn_2SiO_4$) or a relatively complex compound of zinc, oxygen and silicon ($2ZnO.SiO_2$) having the same chemical composition as zinc silicate or a combination of both is formed at such boundary. These crystals tend to become formed in the presence of lead or antimony. These zinc compounds become crystallized in the form of Willemite crystals. Furthermore, crystals of zirconium silicate also become produced at such boundary.

The crystallization of the zirconium silicate occurs in the presence of lead. The crystallization of the zirconium silicate is facilitated by the inclusion of zinc zirconium silicate in the mixture since this compound tends to become dissolved at a lower temperature than zirconium silicate. Zinc zirconium silicate and zirconium silicate tend to exist as natural minerals and are preferably used in this form.

The Willemite crystals are of a different size and shape than the crystals of zirconium silicate. For example, the crystals of zirconium silicate tend to be smaller than the Willemite crystals. This causes nucleations of different sizes to be produced and facilitates the flexing and bending of the crystal layer adjacent the ferrule when subjected to thermal and mechanical shocks. In this way, the hermetic seal is maintained even when the material is subjected to severe thermal or mechanical shocks.

Zirconium spinel tends to increase the mechanical strength of the material. When introduced into the material, zirconium spinel is already in crystalline form so that it does not change as the material is heated and cooled as specified above. As a result, zirconium spinel acts as a filler in the material. Zirconium spinel tends to exist as a natural mineral and is preferably used in this form.

An oxygen valence bond is also produced between the material and the ferrule to facilitate the formation of a hermetic seal between them. This oxygen valence bond results from a chemical bond between oxygen atoms in the material and atoms on the surface of the ferrule 14. In other words, the oxygen is shared by the layer on the surface of the ferrule 14 and the material constituting this invention. This oxygen valence bond is produced during the heating of the material and the ferrule to the relatively high temperatures.

When an alloy of titanium is used as the ferrule 14, the alloy often has a composition of Ti6Al4V. In other words, one (1) molecule of titanium is combined with six (6) molecules of aluminum and four (4) molecules of vanadium. Such an alloy is advantageous because the surface of the alloy tends to form oxides of titanium, vanadium and aluminum and these oxides tend to become bound to the material of this invention by oxygen valence bonding. Thus, the inclusion of the other metals with titanium in the alloy tends to facilitate the hermetic seal with the material of this invention.

Because of the random orientation of the polycrystalline structure and the oxygen valence bonding of the oxygen to the external surface of the ferrule 14, the material does not fragment or crumble in use, even when subjected to thermal and mechanical shocks. For example, any tendency for the material to crack occurs radially toward the terminal pin 12 so as to preserve the characteristics of the material in providing an electrical insulation.

The material constituting this invention is also hermetically sealed to the terminal pin 12. For example, when the terminal pin 12 is made from platinum, the platinum tends to become chemically etched at its surface to a minor extent. This etching occurs from the action on the platinum, during the smelting and fusing operations, of the material constituting this invention. This etching may penetrate the surface of the platinum to a thickness of approximately one half mil (0.0005") to one mil (0.001") when the terminal pin has a thickness of approximately thirty mils (0.030"). The material constituting this invention then tends to become locked in the irregular surface produced in the surface of the terminal pin as a result of such penetration.

The bond between the platinum terminal pin and the material of this invention is actually quite thin in physical dimensions. This bond has a thickness in the order of twenty Angstroms (20 A). The material of this invention at the surface of the platinum terminal pin tends to be more amorphous than the material at the surface of the ferrule 14, particularly when the ferrule is made from titanium or a titanium alloy.

At distances removed from the ferrule 14, the material 13 is more amorphous than at the boundary with the ferrule 14. Thus, the material may be almost entirely crystalline at the boundary with the ferrule 14. However, at positions somewhat removed from the ferrule 14, the material may be predominantly amorphous.

The combination of amorphous and crystalline properties for the material 13 provides certain advantages in addition to those discussed above. For example, the crystalline structure in the material 14 normally has an alpha ($\alpha$) phase at relatively low temperature but the characteristics of the crystalline structure change from the alpha ($\alpha$) phase to the beta ($\beta$) phase as the temperature of the material increases from approximately 800° F. to approximately 1400° F. For example, the coefficient of thermal expansion of the crystalline structure in the beta ($\beta$) phase is different from that in the alpha ($\alpha$) phase.

The partially amorphous characteristics of the material 13 tend to compensate for effects resulting from a transition in the crystalline structure between the alpha ($\alpha$) phase and the beta ($\beta$) phase. The interleaved characteristics of the polycrystalline structure at the boundary with the ferrule 14 also tend to compensate for any changes in the crystalline structure of the material 14 between the alpha ($\alpha$) phase and the beta ($\beta$) phase.

The titanium alloy also has alpha ($\alpha$) and beta ($\beta$) phases. However, these phases are stabilized so that each phase exists over a relatively wide range of temperatures. These different phases are partially instrumental in causing the titanium alloy to be stronger than pure titanium. This is particularly true when the titanium alloy is heat treated.

The phase of the titanium alloy changes from alpha ($\alpha$) to beta ($\beta$) at a temperature of approximately 1300° F. However, a relatively long period of time at a temperature of approximately 1300° F. is required for the titanium alloy to change from the alpha ($\alpha$) phase to the beta ($\beta$) phase. The coefficient of thermal expansion of the titanium alloy in the alpha ($\alpha$) phase is different from that in the beta ($\beta$) phase.

The polycrystalline structure of the material facilitates the retention of a hermetic seal as the titanium alloy changes from the alpha ($\alpha$) phase to the beta ($\beta$) phase. This results from the ability of the polycrystalline layer to adapt to differences in the expansion characteristics of the titanium alloy with changes in temperature. The oxygen valence bond between the ferrule 14 and the material 13 also facilitates the maintenance of the hermetic seal under such circumstances.

The material constituting this invention is highly resistant to strong acids and alkalis. As will be appreciated, this is important when the material is used in a heart pacemaker since the heart pacemaker is generally disposed in the body of a patient and is accordingly subjected to the fluids in the body of the patient.

The material constituting this invention also provides other advantages of some importance. For example, the material provides a high dielectric constant considerably greater than that of most other materials now in use. By way of illustration, the electrical insulation between the terminal pin 12 and the ferrule 14 is a high as $10^{18}$ ohms. This is important in such equipment as heart pacemakers which have to operate satisfactorily under all of the adverse sets of circumstances which a human body is capable of producing.

The material constituting this invention also has other advantages of some importance. For example, when the operation of hermetically sealing the terminal pin 12 and the ferrule 14 has been completed, tests are made to determine if a hermetic seal has actually been produced. If a hermetic seal has not been produced, the combination of the terminal pin, the ferrule and the material may be fused at the temperature of approximately 1225° F. for an additional period to approximately thirty (30) minutes. Since the material is still somewhat amorphous, this additional fusing operation tends to facilitate the creation of the oxygen valence bond between the material and the ferrule. It also tends to facilitate the creation of a polycrystalline structure in the material, particularly at the surface adjacent the ferrule. As a result, any failure to produce a hermetic seal tends to become corrected.

The discussion above has proceeded on the basis of a preferred embodiment. However, all of the advantages discussed above are inherent in the various materials which will be discussed below and which are considered as being included within the invention. For example, a number of different fluxes may be substituted for individual ones of the fluxes discussed above. These fluxes include the following in relative weights of the different materials:

|  | Flux C | Flux D | Flux E | Flux F | Flux G |
|---|---|---|---|---|---|
| Compound |  |  |  |  |  |
| Lead oxide (PbO) | 81.8 | 78.8 | 66.6 | 55.5 | 48.6 |
| Boron oxide ($B_2O_3$) | 10.6 | 9.6 | 18.6 | 3.0 | 6.9 |
| Silicon dioxide ($SiO_2$) | 7.6 | 11.6 | 14.8 | 29.6 | 25.0 |
| Sodium oxide ($Na_2O$) |  |  |  | 4.4 | 3.6 |
| Titanium dioxide ($TiO_2$) |  |  |  | 4.0 | 2.4 |
| Lithium oxide ($Li_2O$) |  |  |  |  | 3.6 |
| Zirconium dioxide ($ZrO_2$) |  |  |  |  | 6.7 |
| Characteristics |  |  |  |  |  |
| Melting Point (°F.) | 850 | 950 | 1050 | 1140 | 1120 |
| Coefficient of Thermal Expansion (in/in × $10^{-7}$) | 104 | 85 | 76 | 90 | 85 |

All of the above materials constitute eutectics for lead borate. The various materials in the flux, other than lead oxide, boric oxide and silicon dioxide, provide additional advantages. For example, the combination of zirconium dioxide and titanium dioxide acts as a pacifier in helping to make the flux compatible with the stuffing material. Furthermore, they tend to facilitate the production of small crystals in the stuffing material. These small crystals facilitate the ability of the material of this invention to withstand thermal and mechanical shocks. The sodium oxide and lithium oxide are advantageous because they tend to reduce the melting temperature of the flux.

Other materials may also be used for the stuffing material in addition to those specified above. Some of the materials are preferable for use in hermetically sealing titanium and others are preferable for use in hermetically sealing alloys of titanium. For example, the following material may be used as the stuffing material, preferably when the member to be sealed is made from titanium:

| Material | Relative Parts By Weight |
|---|---|
| Silicon dioxide ($SiO_2$) | 33.3 |
| Zinc oxide (ZnO) | 33.3 |
| Cobalt oxide (CoO) | 10.0 |
| Zirconium silicate ($ZrSiO_4$) | 15.0 |
| Molybdic oxide ($MoO_3$) | 5.0 |

The cobalt oxide tends to increase the coefficient of thermal expansion of the material to the desired value. The cobalt oxide also imparts a distinctive color to the material and provides an oxygen valence bond to the member such as the ferrule to be hermetically sealed. The molybdic oxide tends to facilitate the bonding of the material to the member to be sealed, particularly when the material is made from titanium or alloys of titanium. The zinc oxide also facilitates the production of the Willemite crystals as described in detail above.

Another material capable of being used for bonding to members made from titanium or alloys of titanium is set forth below:

| Material | Relative Parts by Weight |
| --- | --- |
| Silicon dioxide ($SiO_2$) | 20 |
| Molybdic oxide ($MoO_3$) | 4 |
| Cobalt oxide (CoO) | 3 |
| Lead antimonate | 15 |
| Zinc oxide | 8 |
| Zirconium silicate | 30 |
| Magnesium zirconium silicate | 20 |

The magnesium in the above material initially seeds out to magnesium oxide (MgO) and the magnesium oxide then combines with the silicon dioxide to form magnesium silicon oxide ($MgSiO_3$). This allows an additional amount of zirconium to seed out and form crystals. The antimony enhances the bond to titanium when pure titanium is used and it enhances the bond to titanium, vanadium and aluminum when an alloy of titanium, vanadium and aluminum is used.

Another material capable of being used as the stuffing material has the following composition:

| Material | Relative Parts By Weight |
| --- | --- |
| Cobalt oxide | 31.3 |
| Quartz | 25.6 |
| Zirconium spinel | 14.2 |
| Zinc zirconium silicate | 14.2 |
| Tin oxide | 14.2 |

The material set forth above is preferably used to form hermetic seals with alloys of titanium, vanadium and aluminum. The zinc and the tin help to bond to the titanium, vanadium and aluminum in the alloy.

A further material capable of being used as the stuffing material has the following composition:

| Material | Relative Parts By Weight |
| --- | --- |
| Sodium antimonate ($Na_2O.Sb_2O_5$) | 10 |
| Lead antimonate ($Pb_3(SbO_4)_2$) | 25 |
| Molybdic oxide | 3 |
| Silicon dioxide | 22 |
| Titanium oxide | 2 |
| Zinc zirconium silicate | 38 |

The titanium oxide forms lead titanate with lead oxide. Lead titanate forms long needle-like crystals which are spaced among the crystals of Willemite and zirconium silicate at the boundary between the material and the ferrule. This increases the ability of the polycrystalline structure to withstand temperature and mechanical stresses. It tends to make the material strong mechanically and withstand the propagation of cracks. It also tends to increase the dielectric constant of the material. The molybdic oxide tends to provide a strong oxygen valence bond with the oxygen at the surface of the member to be hermetically sealed.

It will be appreciated that the different oxides in each of the above materials offers the same advantages as those specified above for the same oxides in other materials. For example, the molybdic oxide enhances the bond to titanium when included in each of the materials specified above. Similarly, the cobalt oxide increases the coefficient of thermal expansion and provides coloring when included in each of the materials specified above.

Although the invention has been discussed above in connection with the sealing members constituting electrically conductive metals, the materials of this invention can be used to hermetically seal other materials in addition to those discussed above. For example, the materials can be used to provide hermetic seals to ceramics and glasses. The material can be used to provide hermetic seals to such materials as alumina. When the material is used to provide hermetic seals to ceramics (especially alumina) and glasses, it is provided with a greater proportion of amorphous characteristics than when it is hermetically sealed to titanium or alloys of titanium.

As previously described, the relative proportions of the amorphous and crystalline states are dependent upon the time and temperature of the operations at which the material is heated prior to being fused to the members. The time and temperature are selected in accordance with the characteristics of the materials to be hermetically sealed. For example, the time and temperature are relatively high when a ferrule made from titanium or a titanium alloy is to be sealed to a terminal pin made from platinum since a relatively high proportion of crystalline characteristics is desired in the material to seal the material to titanium. However, when the material is intended to hermetically seal a member made from a ceramic or glass or to seal the material to a terminal pin made from nickel alloys such as "Rene 41" or "Inconel", the combination of time and temperature (and primarily the time) is relatively low in order to preserve a relatively high proportion of amorphous characteristics in the material.

The term "polycrystalline" in the claims is intended to indicate an insulating material formed from a crystalline structure including crystals of at least two different materials. The term "polycrystalline" in the claims is further intended to indicate that the crystals of the different materials have individual parameters and that the crystals of the different materials are intermixed to provide the insulating material with a combination of properties not obtained from the crystals of any single material.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:
1. In combination,
   a first member made from a noble metal,
   a second member made from a material selected from the group consisting of titanium and an alloy of titanium and disposed in spaced relationship to the first member and having at least one of alpha ($\alpha$) and beta ($\beta$) phases, and
   an electrically insulating material preformed to provide partially amorphous and partially crystalline characteristics and hermetically sealing the first and second members and including at least one flux formed from the oxides of lead, silicon and boron, the insulating material being sealed to the first and second members, in at least one of the alpha (α) and beta (β) phases of the second member, by the application of heat to the first and second members and to the insulating material at a particular temperature for a limited period of time, the insulating material having partially amorphous and partially crystalline characteristics in the sealed relationship with the first and second members.

2. The combination set forth in claim 1 wherein the insulating material is particularly crystalline at the boundary with the second member and wherein the insulating material has a coefficient of thermal expansion slightly greater than the coefficient of thermal expansion of the second member.

3. The combination set forth in claim 2 wherein the insulating material has properties of being self-correcting in providing a hermetic seal between the first member and the second member upon an additional application of heat at temperatures less than about 1300° F. when a hermetic seal between the insulating material and each of the first and second members does no exist.

4. The combination set forth in claim 2 wherein the insulating material is formed at temperatures less than about 1300° F. and wherein the insulating material is resistant to acids and alkalies and has an electrical resistance as high as $10^{18}$ ohms.

5. The combination set forth in claim 4 wherein the insulating material includes oxides of at least zinc and zirconium.

6. The combination set forth in claim 5 wherein the insulating material includes the oxide of antimony.

7. The combination set forth in claim 5 wherein the crystals in the insulating material are provided with different sizes and shapes in an intermixed relationship to enhance the flexibility of the insulating material and facilitate resistance to temperature and mechanical shocks.

8. The combination set forth in claim 7 wherein the oxides of zinc and zirconium are in a stuffing having a range by weight of approximately 20% to 45% in the insulating material and the oxides of zinc and zirconium are included in the insulating material respectively in the form of zinc zirconium silicate, zirconium spinel and zirconium silicate.

9. The combination set forth in claim 1 wherein the insulating material is also chemically bound by oxygen valences to the second member and the layer of the insulating material adjacent the second member is provided with crystals of different sizes and shapes to provide a flexibility for withstanding thermal and mechanical shock and wherein the first and second members and the insulating material are heated to a temperature less than 1300° F. for the limited period of time and are then cooled in air after being heated to the temperature less than 1300° F. for the limited period of time.

10. The combination set forth in claim 9 wherein the insulating material has a slightly greater coefficient of thermal expansion than the second member.

11. The combination set forth in claim 9 wherein the insulating material has the properties of providing a hermetic seal to the first and second members upon the application of additional heat to the combination of the first and second members and the insulating material when a hermetic seal has not been previously produced between the first and second members and the insulating material.

12. The combination set forth in claim 1 wherein the insulating material includes crystals of Willemite and crystals formed by the compounds of zirconium, silicon and oxygen and the crystals of Willemite have different sizes and shapes than the crystals formed by compounds of zirconium, silicon and oxygen and the crystals of Willemite and the crystals formed by the compounds of zirconium, silicon and oxygen are concentrated at the boundary with the second member.

13. In combination,
a first member,
a second member spaced from the first member, and
electrically insulating material hermetically sealing the first and second members and including the following in its original composition:
    a first flux consisting of lead oxide, boric oxide and silicon dioxide and having a first melting temperature, and
    a second flux consisting of lead oxide and boric oxide and having a higher melting temperature than the first flux,
a polycrystalline stuffing including oxides of zirconium and zinc and silicon and having properties of providing in a random distribution first crystals having a first size and shape and second crystals having a second size and shape different from the first size and shape, the first and second crystals being primarily disposed in a layer adjacent to at least a particular one of the first and second members to provide a flexibility resisting thermal and mechanical shock, the first and second members and the first and second fluxes and the polycrystalline stuffing being hermetically sealed by the application of heat at a temperature less than 1300° F. for a limited period of time and by subsequent cooling in air.

14. The combination set forth in claim 13 wherein the polycrystalline stuffing includes zinc oxide in the form of compounds with silicon dioxide and wherein the insulating material has properties of providing Willemite in the layer adjacent at least the particular one of the first and second members and wherein the first and second members, the first and second fluxes and the polycrystalline stuffing are heated to the temperature less than 1300° F. for a limited period less than one half (½) hour.

15. The combination set forth in claim 14 wherein the insulating material is more amorphous at positions removed from the particular one of the first and second members than at the boundary of the particular one of the first and second members and wherein the material has self-correcting properties of producing a hermetic seal with the first and second members, upon a previous failure to produce a seal with the first and second members, by reheating the first and second members and the insulating material to a temperature less than 1300° F. for a limited period of time.

16. The combination set forth in claim 15 wherein the insulating material is formed at temperatures below about 1300° F. and the first member is made from a noble metal and the second member is made from a material selected from the group consisting of titanium and a titanium alloy and the insulating material is provided with a coefficient of thermal expansion slightly greater than that of the second member.

17. The combination set forth in claim 13 wherein the insulating material is formed at temperatures below about 1300° F.

18. The combination set forth in claim 17 wherein the first member is made from a noble metal and the second member is made from a material selected from the group consisting of titanium and a titanium alloy.

19. The combination set forth in claim 18 wherein the second flux has a greater percentage by weight in the insulating material than the first flux and the polycrystalline stuffing has a higher melting temperature than the melting temperatures of the first and second fluxes.

20. In combination, a first member, a second member, and an electrically insulating material preformed to provide partially polycrystalline and partially amorphous properties and hermetically sealing the first and second members and having a polycrystalline layer at a position adjacent the second member and an oxygen valence bond to the second member and being more amorphous at positions removed from the second member than at the boundary of the second member, the insulating material being hermetically sealed to the first and second members by heating the first and second members and the insulating material at temperatures less than about 1300° F. for a limited period of time and by cooling the first and second members and the insulating material in air.

21. The combination set forth in claim 20 wherein the polycrystalline layer adjacent the second member includes Willemite crystals and crystals constituting compounds of zirconium.

22. The combination set forth in claim 21 wherein the insulating material has self-correcting properties, upon a failure to provide a hermetic seal with the first and second members, by reheating the first and second members and the insulating material to a temperature less than 1300° F. for a limited period of time and by subsequently recooling the first and second members and the insulating material in air.

23. The combination set forth in claim 20 wherein the surface of the first member is etched and the insulating material is retained within the etchings in the surface of the first member and wherein the limited period for the heating of the first and second members and the insulating material to a temperature less than 1300° F. is less than one half (½) hour.

24. In combination, a first member made from a noble metal, a second member displaced outwardly from the first member and made from a material selected from the group consisting of titanium and a titanium alloy, and an insulating material preformed to provide partially amorphous and partially polycrystalline characteristics and directly engaging the first and second members and hermetically sealing the first and second members by the application of heat at a particular temperature for a limited period of time and having a partially amorphous and partially crystalline composition in the hermetically sealed relationship with the first and second members and having a primarily polycrystalline composition at the boundary with the second member.

25. The combination set forth in claim 24 wherein an oxygen valence bond exists between the insulating material and the second member.

26. The combination set forth in claim 24 wherein the surface of the first member is etched and the insulating material is bound in the etched surface of the first member and the insulating material has a slightly greater coefficient of expansion than the second member.

27. The combination set forth in claim 26 wherein the polycrystalline composition at the boundary between the second member and the insulating material is produced by a mixture of oxides of zinc and zirconium.

28. The combination set forth in claim 24 wherein the insulating material has self-correcting properties of providing a hermetic seal to the first and second members upon the application of additional heat, at a temperature less than 1300° F. for a limited period of time, to the combination of the first and second members and the insulating material when a hermetic seal has not been previously produced.

29. The combination set forth in claim 24 wherein the surface of the first member is etched and the insulating material is bound in the etched surface of the first member and wherein the first and second members and the insulating material are heated to a temperature less than 1300° F. for the limited period of time and are then cooled in air to obtain a hermetically sealed relationship between the insulating material and the first and second members.

30. The combination set forth in claim 24 wherein the insulating material has a slightly greater coefficient of expansion than the second member and wherein the particular temperature is less than 1300° F. and wherein the limited period of time for the application of heat at the temperature less than 1300° F. is less than one half (½) hour.

31. The combination set forth in claim 24 wherein the polycrystalline composition at the boundary between the second member and the insulating material is produced by a mixture of oxides of zinc and zirconium.

32. In combination, a first member, a second member separated from the first member, and an electrically insulating material preformed to provide partially amorphous and partially polycrystalline properties and hermetically sealing the first and second members and having self-correcting properties of providing a hermetic seal between the first and second members by the application of heat to the combination of the first and second members and the insulating material at temperatures less than about 1300° F. for a limited period of time when a hermetic seal does not exist, the insulating material being partially amorphous and partially crystalline in the hermetically sealed relationship with the first and second members and being more crystalline at the boundary between the second member and the insulating material than at positions removed from such boundary.

33. The combination set forth in claim 32 wherein the insulating material is primarily polycrystalline at the boundary between the second member and the insulating material and the polycrystals have a random orientation of different sizes and shapes to provide a flexibility in withstanding thermal and mechanical shocks and wherein the first and second members and the insulating material are cooled in air after being heated to the temperature less than 1300° F. for the limited period of time.

34. The combination set forth in claim 33 wherein the polycrystals at the boundary between the second member and the insulating material comprise a mixture of oxides of zinc and zirconium and wherein the limited period for heating the first and second members and the insulating material to the temperature less than 1300° F. is less than one half (½) hour.

35. The combination set forth in claim 33 wherein the surface of the first member is etched and the insulating material is locked in the etched surface of the first member and the insulating material includes the oxides of silicon, boron and lead.

36. The combination set forth in claim 35 wherein the insulating material has a slightly greater coefficient of thermal expansion than the second member and the insulating material includes a first flux having a relative percentage by weight of approximately 15% to 25% by weight and a second flux having a relative percentage of approximately 40% to 55% by weight and a crystal stuffing material providing the remaining percentage by weight and wherein the first flux has the following composition by weight:

| Material | Relative % By Weight |
| --- | --- |
| Lead Oxide | 68.5 |
| Boric Oxide | 10.5 |
| Silicon Dioxide | 21.0 | and the second flux has the following composition by weight:

| Material | Relative % By Weight |
| --- | --- |
| Lead Oxide | 80.0 |
| Boric Oxide | 20.0 |

37. The combination set forth in claim 36 wherein the crystal stuffing material has the following composition:

| Material | Relative % By Weight |
| --- | --- |
| Cobalt Oxide | 31.3 |
| Quartz | 25.6 |
| Zirconium Spinel | 14.2 |
| Zinc Zirconium Silicate | 14.2 |
| Tin Oxide | 14.2 |

38. The combination set forth in claim 36 wherein the crystal stuffing material has the following composition:

| Material | Relative % By Weight |
| --- | --- |
| Silicon Dioxide | 20 |
| Molybdic Oxide | 4 |
| Cobalt Oxide | 3 |
| Lead Antimonate | 15 |
| Zinc Oxide | 8 |
| Zirconium Silicate | 30 |
| Magnesium Zirconium Silicate | 20 |

39. The combination set forth in claim 36 wherein the crystal stuffing material includes lead antimonate, zinc zirconium silicate, zirconium spinel and zirconium silicate.

40. The combination set forth in claim 36 wherein the crystal stuffing material has the following composition:

| Material | Relative % By Weight |
| --- | --- |
| Lead Antimonate | 2 |
| Zinc Zirconium Silicate | 1 |
| Zirconium Spinel | 1 |
| Zirconium Silicate | 1 |

41. The combination set forth in claim 40 wherein the first member is made from a noble metal and the second member is made from a material selected from the group consisting of titanium and a titanium alloy.

42. The combination set forth in claim 35 wherein the first member is made from a noble metal and the second member is made from titanium in at least one of the alpha ($\alpha$) and beta ($\beta$) phases.

43. The combination set forth in claim 32 wherein the first member is made from a noble metal and the second member is made from a material selected from the group consisting of titanium and an alloy of titanium.

44. In combination in a heart pacemaker,
a terminal pin made from a noble metal,
a ferrule made from a material selected from the group consisting of titanium and an alloy of titanium, and
a material hermetically sealing the terminal pin and the ferrule and having insulating properties,
the insulating material being partially amorphous and partially crystalline and being particularly crystalline at the boundary with the ferrule,
oxides of lead, boron and silicon being included in the insulating material in a first flux and oxides of lead and boron being included in the insulating material in a second flux having a higher melting temperature than the first flux and oxides of lead, zinc, antimony and zirconium being included in the insulating material in a crystalline stuffing and the first flux being included in the insulating material with a weight of approximately 15% to 25% and the second flux being included in the insulating material with a weight of approximately 40% to 55% and the crystalline stuffing constituting the remainder of the insulating material.

45. In combination,
a first member,
a second member spaced from the first member, and
an insulating material disposed between the first and second members and hermetically sealing the first and second members and formed from:

(a) a first flux consisting of lead oxide, silicon dioxide and boric ocide and having a first melting temperature, (b) a second flux consisting of lead oxide and boric oxide and having a higher melting temperature than the first flux, and (c) a crystalline stuffing including oxides of zirconium and zinc and silicon and having properties of providing crystals in a layer adjacent to at least a particular one of the first and second members, the insulating material being formed at temperatures below about 1300° F. and the first member being made form a noble metal and the second member being made from a material selected from the group consisting of titanium and a titanium alloy and the insulating material being provided with a coefficient of thermal expansion slightly greater than that of the second member.

46. The combination set forth in claim 45 wherein the first flux is formed from the following materials:

| Material | Relative % By Weight |
| --- | --- |
| Lead Oxide | 68.5 |
| Boric Oxide | 10.5 |
| Silicon Dioxide | 21.0 | and the second flux is formed from the following materials:

| Material | Relative % By Weight |
| --- | --- |
| Lead Oxide | 80.0 |
| Boric Oxide | 20.0 |

47. In combination,
a first member,
a second member separated from the first member, and
insulating material hermetically sealing the first and second members and having self-correcting properties of providing a hermetic seal between the first and second members by the application of heat to the combination of the first and second members and the insulating material when a hermetic seal does not exist,
the insulating material being primarily polycrystalline at the boundary between the second member and the insulating material and the polycrystals having a random orientation of different sizes and shapes to provide a flexibility in withstanding thermal and mechanical shocks and the insulating material being progressively amorphous from the boundary between the second member and the insulating material,
the surface of the first member being etched and the insulating material being locked in the etched surface of the first member,
the insulating material including first and second fluxes each including boric oxide, the first and second fluxes forming eutectics to effectively decrease the melting temperature of the boric oxide in the fluxes.

48. In combination,
a first member,
a second member disposed in spaced relationship to the first member, and
an electrically insulating material preformed to a partially amorphous and partially polycrystalline structure with the amorphous and polycrystalline structure being intermixed, the insulating material being disposed between the first and second members and the first and second members and the insulating material being heated at a temperature below 1300° F. for a limited period of time to hermetically seal the first and second members and the insulating material.

49. The combination set forth in claim 48 wherein the first member is made from a noble metal and the second member is made from a material selected from the group consisting of titanium and a titanium alloy and the first and second members and the insulating material are cooled in air after being heated to the temperature less than 1300° F. for the limited period of time.

50. The combination set forth in claim 49 wherein the material is more crystalline at the boundary between the second member and the insulating material than at positions removed from such boundary after being heated with the first and second members to the temperature less than 1300° F. for the limited period of time and the insulating material is directly sealed to the first and second members.

51. The combination set forth in claim 50 wherein the surface of the first member is etched by the heating of the first and second members and the insulating material to the temperature less than 1300° F. for the limited period of time and the insulating material is locked in the etched surface of the first member by such heating.

52. The combination set forth in claim 50 wherein the insulating material is formed from the oxides of silicon, boron, lead, zinc and zirconium and the limited period of time for the heating of the first and second members and the insulating material to the temperarture less than 1300° F. is less than one half ($\frac{1}{2}$) hour.

53. The combination set forth in claim 48 wherein the insulating material includes,
a first flux having the following composition:

| Material | Relative % By Weight |
| --- | --- |
| Lead Oxide | 68.5 |
| Boric Oxide | 10.5 |
| Silicon Dioxide | 21.0 | and a second flux having the following composition:

| Material | Relative % By Weight |
| --- | --- |
| Lead Oxide | 80.0 |
| Boric Oxide | 20.0 | and a crystal stuffing including the oxides of zinc, zirconium and silicon,
the first flux being included in the insulating material in the range of approximately 15% to 25% by weight and the second flux being included in the insulating material in the range of approximately 40% to 55% by weight and the remainder of the insulating material being constituted by the crystal stuffing.

54. The combination set forth in claim 53 wherein the crystal stuffing has the following composition:

| Material | Relative % By Weight |
|---|---|
| Lead Antimonate | 2 |
| Zinc Zirconium Silicate | 1 |
| Zirconium Spinel | 1 |
| Zirconium Silicate | 1 |

55. The combination set forth in claim 53 wherein the crystal stuffing has the following composition:

| Material | Relative Parts By Weight |
|---|---|
| Silicon Dioxide | 33.3 |
| Zinc Oxide | 33.3 |
| Cobalt Oxide | 10.0 |
| Zirconium Silicate | 15.0 |
| Molybdic Oxide | 5.0 |

56. The combination set forth in claim 48 wherein the insulating material includes at least one flux having at least one of the following compositions:

| | Relative Parts By Weight | | | | |
|---|---|---|---|---|---|
| | Flux C | Flux D | Flux E | Flux F | Flux G |
| Compound | | | | | |
| Lead oxide (PbO) | 81.8 | 78.8 | 66.6 | 55.5 | 48.6 |
| Boron Oxide (B$_2$O$_3$) | 10.6 | 9.6 | 18.6 | 3.0 | 6.9 |
| Silicon dioxide (SiO$_2$) | 7.6 | 11.6 | 14.8 | 29.6 | 25.0 |
| Sodium oxide (Na$_2$O) | | | | 4.4 | 3.6 |
| Titanium dioxide (TiO$_2$) | | | | 4.0 | 2.4 |
| Lithium oxide (Li$_2$O) | | | | | 3.6 |
| Zirconium dioxide (ZrO$_2$) | | | | | 6.7 |
| Characteristics | | | | | |
| Melting Point (°F.) | 850 | 950 | 1050 | 1140 | 1120 12 |
| Coefficient of (in/in × 10$^{-7}$) | 104 | 85 | 76 | 90 | 85 |

57. The combination set forth in claim 56 wherein the insulating material includes a crystal stuffing having the following composition:

| Material | Relative Parts By Weight |
|---|---|
| Lead Antimonate | 2 |
| Zinc Zirconium Silicate | 1 |
| Zirconium Spinel | 1 |
| Zirconium Silicate | 1 |

58. The combination set forth in claim 56 wherein the insulating material includes a crystal stuffing having the following composition:

| Material | Relative Parts By Weight |
|---|---|
| Silicon Dioxide | 33.3 |
| Zinc Oxide | 33.3 |
| Cobalt Oxide | 10.0 |
| Zirconium Silicate | 15.0 |
| Molybdic Oxide | 5.0 |

59. The combination set forth in claim 56 wherein the insulating material includes a crystal stuffing having the following composition:

| Material | Relative Parts By Weight |
|---|---|
| Cobalt Oxide | 31.3 |
| Quartz | 25.6 |
| Zirconium Spinel | 14.2 |
| Zinc Zirconium Silicate | 14.2 |
| Tin Oxide | 14.2 |

60. The combination set forth in claim 56 wherein the insulating material includes a crystal stuffing having the following composition:

| Material | Relative Parts By Weight |
|---|---|
| Silicon Dioxide | 20 |
| Molybdic Oxide | 4 |
| Cobalt Oxide | 3 |
| Lead Antimonate | 15 |
| Zinc Oxide | 8 |
| Zirconium Silicate | 30 |
| Magnesium Zirconium Silicate | 20 |

61. The combination set forth in claim 48 wherein the insulating material includes the oxides of silicon, boron and lead and the limited period of time for the heating of the first and second members and the insulating material to the temperature less than 1300° F. is less than one half (½) hour.

* * * * *